(12) United States Patent
Zhang et al.

(10) Patent No.: US 9,507,915 B2
(45) Date of Patent: Nov. 29, 2016

(54) MANAGING THE DELIVERY OF ALERT MESSAGES BY AN INTELLIGENT EVENT NOTIFICATION SYSTEM

(71) Applicants: Yihan Zhang, Thornhill (CA); Tim Chant, Bradford (CA)

(72) Inventors: Yihan Zhang, Thornhill (CA); Tim Chant, Bradford (CA)

(73) Assignee: Globestar Systems Inc., Toronto (CA)

( * ) Notice: Subject to any disclaimer, the term of this patent is extended or adjusted under 35 U.S.C. 154(b) by 0 days.

(21) Appl. No.: 14/525,851

(22) Filed: Oct. 28, 2014

(65) Prior Publication Data

US 2016/0117901 A1    Apr. 28, 2016

(51) Int. Cl.
*G08B 23/00* (2006.01)
*G06F 19/00* (2011.01)

(52) U.S. Cl.
CPC ......... *G06F 19/345* (2013.01); *G06F 19/3418* (2013.01)

(58) Field of Classification Search
CPC ............ G06F 19/3406; G06F 19/327; G06F 19/345; G06F 19/3418; G08B 21/043
USPC ............ 340/573.1, 539.12, 539.13; 600/300, 600/301
See application file for complete search history.

(56) References Cited

U.S. PATENT DOCUMENTS

| | | | | |
|---|---|---|---|---|
| 7,920,061 B2* | 4/2011 | Klein | .................... | A61B 5/1113 340/573.1 |
| 8,878,676 B2* | 11/2014 | Koblasz | ............ | G08B 21/0261 340/573.1 |
| 2009/0091458 A1* | 4/2009 | Deutsch | ................ | G06F 19/327 340/573.1 |
| 2012/0075464 A1* | 3/2012 | Derenne | .............. | A61B 5/0013 600/595 |
| 2014/0320290 A1* | 10/2014 | Reeder | ................. | A61B 5/0002 340/573.1 |

* cited by examiner

*Primary Examiner* — Thomas Mullen
(74) *Attorney, Agent, or Firm* — Robert Schuler

(57) ABSTRACT

A healthcare system includes an event notification system (ENS) and a real-time location (RTL) system. The ENS operates to receive event messages from an event generation device that includes the identity of a clinical event instance, the location of the clinical event source and timestamp information associated with the event, and it operates to receive tag message information that includes the identity of a caregiver associated with the tag, the current location of the tag and timestamp information. Alert message logic operates on the clinical event information and the tag information to determine whether an alert message should be sent to a caregiver currently attending to a patient.

25 Claims, 6 Drawing Sheets

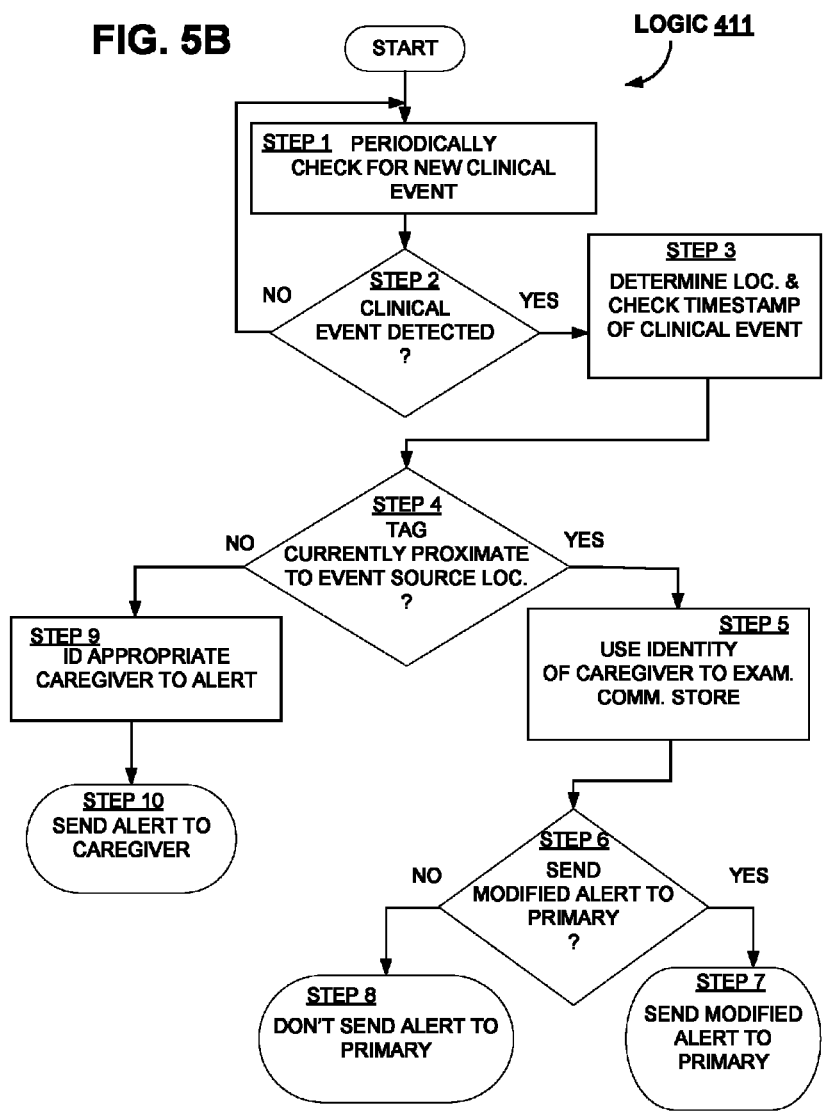

MANAGING THE DELIVERY OF ALERT MESSAGES BY AN INTELLIGENT EVENT NOTIFICATION SYSTEM

FIELD OF THE INVENTION

The present disclosure relates to an event notification system that manages the sending of alert messages to a caregiver as the result of receiving clinical information from monitoring equipment associated with a patient and depending upon the proximity of the caregiver to the patient.

BACKGROUND

In certain settings, it is necessary to initiate a request for assistance that is automatically distributed to an appropriate individual. Systems are in use that are able to receive event messages from one or more event generation devices, process the event message to identify which of one or more individuals should receive a message alerting them to the event occurrence, and to transmit an alert message to the identified individual(s) in an appropriate format. These systems are typically referred to as Event Notification Systems (ENS), and they can be useful in healthcare settings, emergency management settings, retail or commercial settings, and in many other settings. For the purposes of this description, an ENS will be described in the context of a healthcare setting.

FIG. 1 is a diagram illustrating a healthcare network 100 that comprises an Event Generation Device (EGD) 110 and an Event Notification System 120 (ENS) connected over a network to a healthcare server 115. The EGD 110 can be in communication via a wired or wireless network link with the server 115, and the ENS 120 can be in communication with an alert message recipient (AMR) 130 over a wired or wireless link. In a hospital setting the AMR 130 can be any member of a hospital staff, such as a doctor, a nurse or other caregiver. In a hospital setting, the EGD 110 can be, among other things, a piece of equipment such as a heartbeat, blood pressure, temperature, blood oxygen, or respiration monitor. It can be a communication device located in an emergency department bay or intensive care unit operated by staff for the purpose of requesting supplies or other staff, or it can be a nurse station. Each EGD 110 can generate and transmit event messages that comprise the identity of the originating device, the time the message is transmitted and information particular to the purpose of the alert message, such as a request for supplies, a request for a staff member, or clinical information such as an indication that a particular patient's heart has stopped. Each different type of event can be identified by a code that is standard to the environment in which the device is operating. The ENS 120 generally operates to, among other things, receive event messages and to examine their contents to determine which particular device sent the message and to determine which recipient or recipients an alert message should be forwarded to. In a healthcare or other setting, it is often important to identify and to alert a caregiver or caregivers closest to the source of an event of the event's occurrence to provide prompt responses. FIG. 2 is a diagram of a healthcare network 200 having functionality that operates to receive information from either or both of a patient monitor 201 and some other type of event generation device 202, such as the EGD in FIG. 1, and to receive real-time location information from a real-time location (RTL) system 210 all for the purpose of determining the proximity of a caregiver to the source of a clinical event associated with a particular patient.

The healthcare network 200 of FIG. 2 can be implemented in one or more computer servers 205 or other type of computational device which is capable of communicating with a network (local or wide-area network) and is configured to include some or all of the functionality comprising the healthcare network 100 described earlier with reference to FIG. 1. Additionally, the network 200 also comprises an RTL system 210 in communication with a plurality of tag detection devices 220. Each of the RTL tag detectors can operate to receive signals from any of a plurality of wireless RTL tags 230, that can be attached to an individual or to a piece of equipment, and to transmit information (tag ID for instance) in the signals received from a tag over a network link to the RTL system 210. The tag detection device 220, or simply detector 220, can be strategically positioned to detect the presence of a tag 230 within range of the detector in some or all of a plurality of specified facility locations. These locations can correspond to particular buildings, floors, hallways, rooms or other specified locations in a particular facility. The RTL system 210 is also comprised of a listing of tag identities 215 and a listing of tag detector locations 225, wherein the tag identity 215 can be unique coded information specified by a system administrator, and each tag detector location 225 can correspond to an actual, physical location within a building, such as a particular floor, a hallway, a room, etc. The tag detector locations 225 can be stored in any suitable non-volatile memory (not shown) comprising the healthcare network 200. The RTL system 210 can be designed to operate with either active or passive location tags. In the case where the system is operating with passive tags, the system includes a transceiver that periodically sends out a signal that activates circuitry in the passive tag causing it to transmit tag information (typically a tag ID) back to the system 210. In the case of active tags, each tag includes a battery to power transmitter circuitry that operates to periodically transmit a signal that includes, among other things, the identity of that tag. In operation, a tag worn by a staff member or attached to a piece of mobile medical equipment comes into range of a tag detector 220 which detects the presence and identity of the tag and transmits the tag ID and detector location ID to the RTL system 210, which then stores the current tag location and the time of detection in non-volatile memory associated with the healthcare network 200 for later use.

In addition to the RTL system 210 described with reference to FIG. 2, the network 200 also comprises an event notification system (ENS) 240 similar to the system 120 described earlier with reference to FIG. 1. In addition to the functionality comprising the ENS 120, ENS 240 can have proximity notification functionality 250 that operates to detect one or more appropriate staff members closest to the source of an event, and to notify the one or more identified staff members of the event and the location of the event.

BRIEF DESCRIPTION OF THE DRAWINGS

The present invention can be best understood by reading the specification with reference to the following figures, in which:

FIG. 5B is a flow diagram illustrating the operation of another embodiment of alert message logic comprising the notification function of FIG. 4.

DETAILED DESCRIPTION

Figure 1:
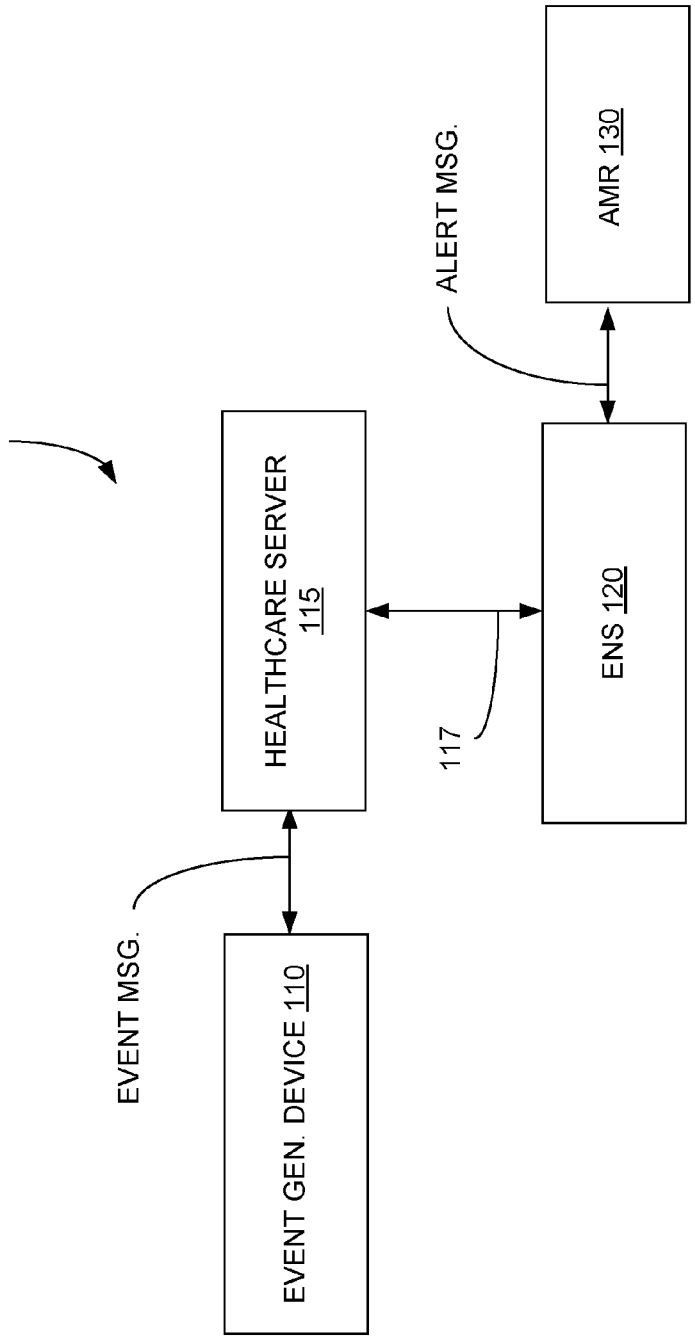
FIG. 1 is a diagram of a healthcare network 100.
Figure 2:
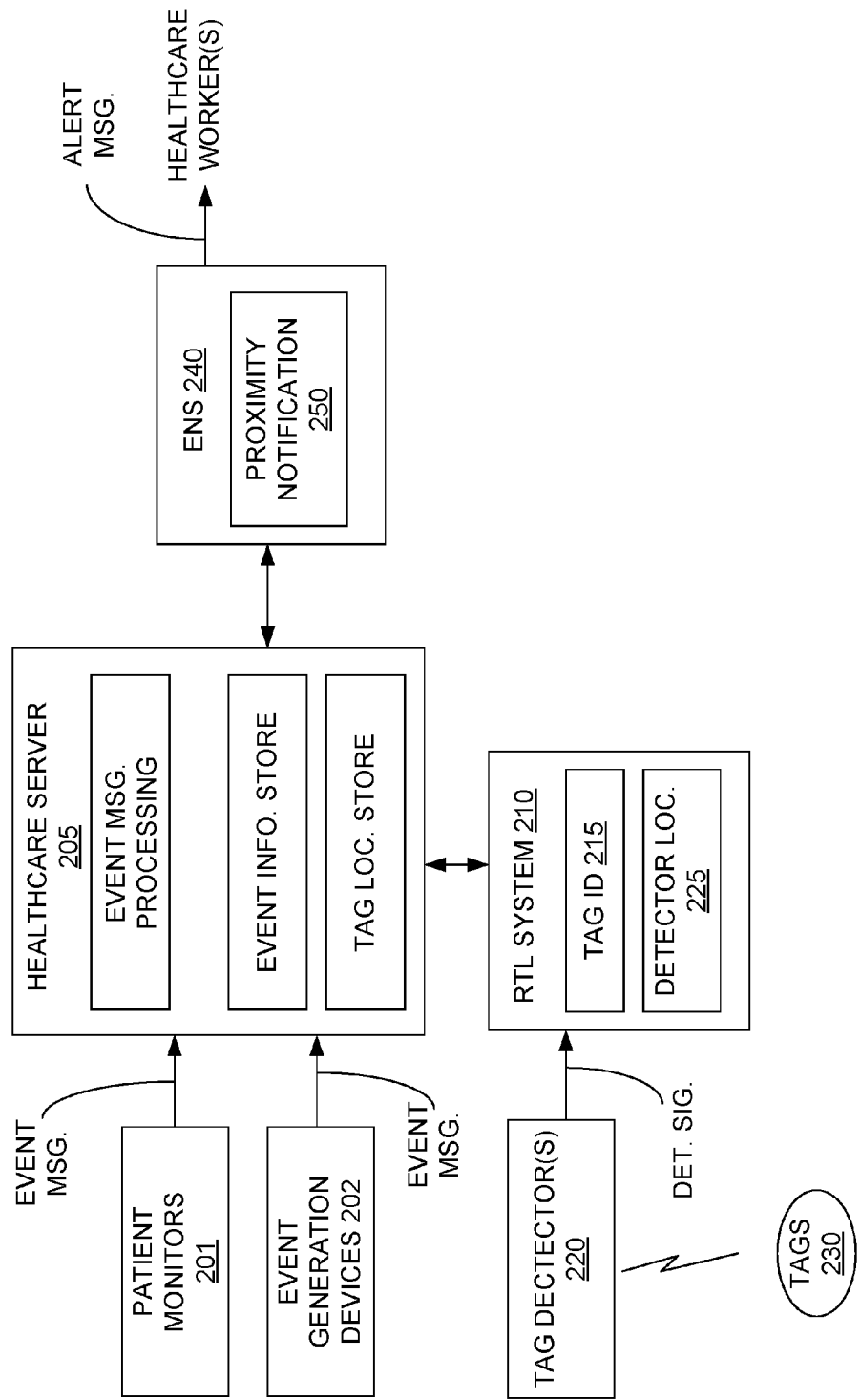
FIG. 2 is a diagram of a healthcare network 200 having location detection and proximity notification functionality.

During the time that a caregiver is attending to a patient, it can be distracting for that caregiver to receive an alert message, from an event notification system, that is generated as the result of a clinical event being detected by a monitor associated with the very same patient. Patient monitors are typically configured to emit an audible indication when they detect a clinical event, and this audible indication alerts a caregiver proximate to the patient of the clinical event. Typically, the same caregiver also receives an alert message (on some mobile communication device) that is generated as the result of the same clinical event. This alert message is redundant or superfluous information that can often distract the caregiver from attending to the patient.

In order to overcome this distraction, we found that it is possible to prevent an event notification system from sending an alert message to a caregiver if a monitor associated with a patient detects a clinical event while the caregiver is proximate or attending to that patient. In normal operation, when it detects a clinical event, an event notification system generates and sends an alert message to a caregiver regardless of their proximity to a patient (i.e., whether the caregiver is attending the patient or not). However, and according to the invention, if a patient monitor detects a clinical event during the time that a caregiver is attending to the patient, an event notification system operates to not send an alert message to the caregiver.

In an alternative embodiment, a standard alert message can only be sent to a secondary communication device not worn by the caregiver, such as a nurse station or the caregiver's computer, or some other mobile or stationary communication device that can be in communication with a healthcare network.

In another embodiment, a modified alert message can be sent to the primary communication device worn by the caregiver if a monitor associated with a patient detects a clinical event while the caregiver is proximate or attending to the patient. When played by the caregiver's primary communication device, the modified alert message exhibits an audible or physical characteristic that can be heard or sensed by the caregiver but does not distract the caregiver from attending to the patient. According to this embodiment, the alert message can comprise instructions that cause a communication device worn by a caregiver to play a distinctive sound or cause it to vibrate in a distinctive manner that is different than a standard alert message. The modified alert message played by the device can be characterized by, but not limited to, a tone that has a lower volume level than a standard alert message, it can be characterized by a unique tonal pattern, a reduced vibratory intensity or vibratory pattern, or characterized by a normal ring tone followed by one or more distinctive ring tone patterns.

Implementing any of the embodiments described above can result in an improved level of clinical care in many patient care environments by allowing a caregiver to fully focus their attention to a patient they are currently attending without receiving redundant, unnecessary or distracting alert messages associated with a clinical condition this patient is experiencing. Various embodiments of our invention are now described below with reference to the figures.

Figure 3:
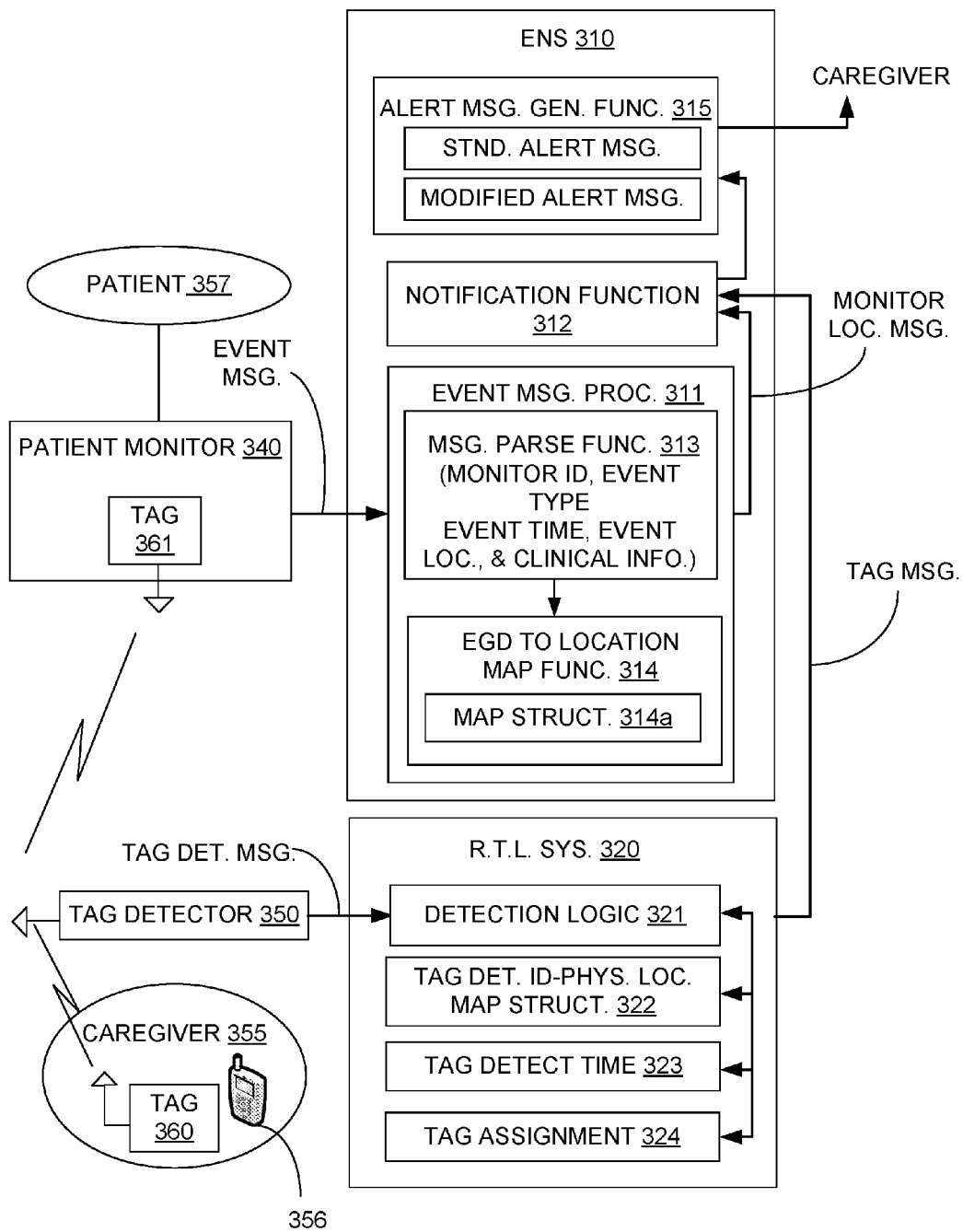
FIG. 3 is a diagram illustrating one embodiment of a healthcare network 300.

FIG. 3 is a diagram showing a portion of a healthcare network 300 comprising, among other things, an event notification system (ENS) 310, an RTL system 320, one or more patient monitors or event generation devices 340 (connected to one or more associated patients 357) and one or more caregivers 355 with associated tags 360 and communication devices 356. It should be understood that the healthcare network 300 shown in FIG. 3 is abridged to show only those elements that can be employed to implement the invention. A typical healthcare network can have many more elements, such as one or more network servers some or all of which can configured to receive information from various clinical departments or individuals or from other systems that are operating in the same network environment.

The ENS 310 and RTL system 320 functionality of FIG. 3 can be implemented in computer program code stored in a non-volatile memory device associated with the same or different computational devices that are connected to the healthcare network. The computational device(s) can be a network server described above or any other device that is suitable for running the computer program code and for communicating over the healthcare network with other devices and functionality comprising the network. The ENS 310 is connected over a wired or wireless network link to one or more event generation devices (EGD) 340 (which in this case is shown as a patient monitor) that detects clinical events relating to a patient's physiology. While the embodiment described herein uses a patient monitor, the EGD can be any device that generates and sends an event message, such as a nurse call station, an emergency room or operating room communication device, or any other device that operates to generate an event message. Such an event message can comprise the identity of the EGD (EGD.ID), the type of event (cardiac, blood oxy., respiratory, etc.), patient clinical/physiological information pertaining to the event type (HB rate, blood oxy. level, respiratory frequency), and it can have information associated with a time (time stamp) that the event is detected. The event message can be transmitted over a wireless or wired link to the ENS 310 where event message processing functionality 311 operates on the message information. Specifically, the message processing function 311 has an event message parsing function 313 that operates to parse information in the message and examines the parsed event message information to determine the identity of the particular EGD, which in this case is any one of a plurality of patient monitors 340, to determine the event type, and to identify patient clinical information. The function 311 also operates to parse and examine the event message for a time stamp to determine the time the patient clinical event occurred. After parsing an event message, the parsing function can send information associated with a unique identity of a patient monitor (serial number for instance) to an EGD-to-physical location map function 314, and the function 314 can use the unique identity of the patient monitor to look up the physical location of the monitor in a map structure 314a associated with this function. The map function 314 is only used to determine the location of a patient monitor that is in a fixed position (i.e., attached to a room wall) within a care facility. This monitor location information can be sent to a notification function 312 in a monitor location message. If the position of the monitor changes, a system administrator can change the information in the map structure to reflect the changed position of the patient monitor. This map structure 314a is comprised of room numbers (or some other appropriate physical location identification) and the identity of each patient monitor located at that room number. Information associated with the patient monitor identity and location, type of clinical event and associated clinical information, and the time stamp associated with the clinical event can then be sent to the notification function 312.

The patient monitor 340 in FIG. 3 can either be a fixed position device, as described earlier, or it can be a mobile device (can be moved from location to location as needed in a care facility). In the case that the patient monitor is mobile, it can have an RTL tag 361, either active or passive, that can be detected by or is communicated with by a tag detector 350 connected in some manner to the healthcare network 300. Each tag detector 350 can operate to detect the presence of one or more tags 360 worn by a staff member or attached to a mobile patient monitor for example. When a tag 360 comes into range of a tag detector 350, the tag detector operates to request unique tag ID information stored on the tag, and send a message to the RTL system 320 that comprises the unique tag ID information, the identity of the tag detector and the time that the tag is detected. The RTL system 320 can have detection logic 321, a tag.id to physical location map structure 322, and a tag detection time store 323. The detection logic 321 generally operates to receive the tag detector message and to examine the message for a unique tag detector ID, information corresponding to an identity of the tag (tag.id), and the time at which the tag is detected. Using the tag identity, the logic 321 accesses the map structure 322 to determine the current physical location within the care facility, and the logic 321 accesses a tag assignment record to determine which caregiver is assigned to wear the tag. The physical location identified as being the current location of the tag, the unique tag ID, the identity of the caregiver wearing the tag and the detection time can be sent over a network link to the notification logic 312 in a Tag Message.

Continuing to refer to FIG. 3, the notification function 312 comprises logical instructions that, among other things, operate on information comprising a tag message received from the RTL system 320 and operates on information comprising a monitor location message to determine whether a patient clinical event occurs during the time the caregiver is attending to the patient. In the event that a clinical event is detected during the time that the caregiver is attending the patient, the notification function 312 can either not send a message to an alert message generation function 315 (and consequently no alert message is generated), or it can send a message to the generator 315 that includes instructions that causes this function to send a standard alert message to one or more of the caregiver's communications devices that are designated as other than a primary device, or it can send a message to the alert message generator that has instructions which cause the generator to send a modified alert message to a selected/configured one or more of the caregiver's communication devices. Managing alert messages in this manner allows a caregiver to focus their attention to attending their patient as opposed to constantly checking for alerts that only convey redundant information about their patient.

Typically, a standard alert message sent to a caregiver's primary communication device comprises annunciation instructions that when operated on by the device cause it to play one or more tones, some combination of tones or to vibrate at a particular frequency and intensity or behave in some manner that attracts the wearer's attention. In an alternative embodiment, and in the case that a caregiver is attending a patient while a monitor associated with the patient detects a clinical event, the ENS 310 can be configured to send a modified alert message to a caregiver. This modified alert message comprises annunciation instructions that when operated on by the caregiver's communication device cause it to play audible sounds or to vibrate in a manner that is recognizably different, and that is implicitly recognized by the caregiver as annunciating an alert generated as the result of a clinical event associated with the patient they are currently attending.

As described earlier with reference to FIG. 3, logical instructions comprising the notification function 312 operate on information comprising a monitor location message and on information comprising a tag message to determine whether or not an alert message is generated, and if generated to which of one or more individuals the alert is sent, and it determines what type of alert message is sent to each individual. A more detailed description of the operation and elements comprising the notification function 312 follows with reference to FIG. 4.

Figure 4:
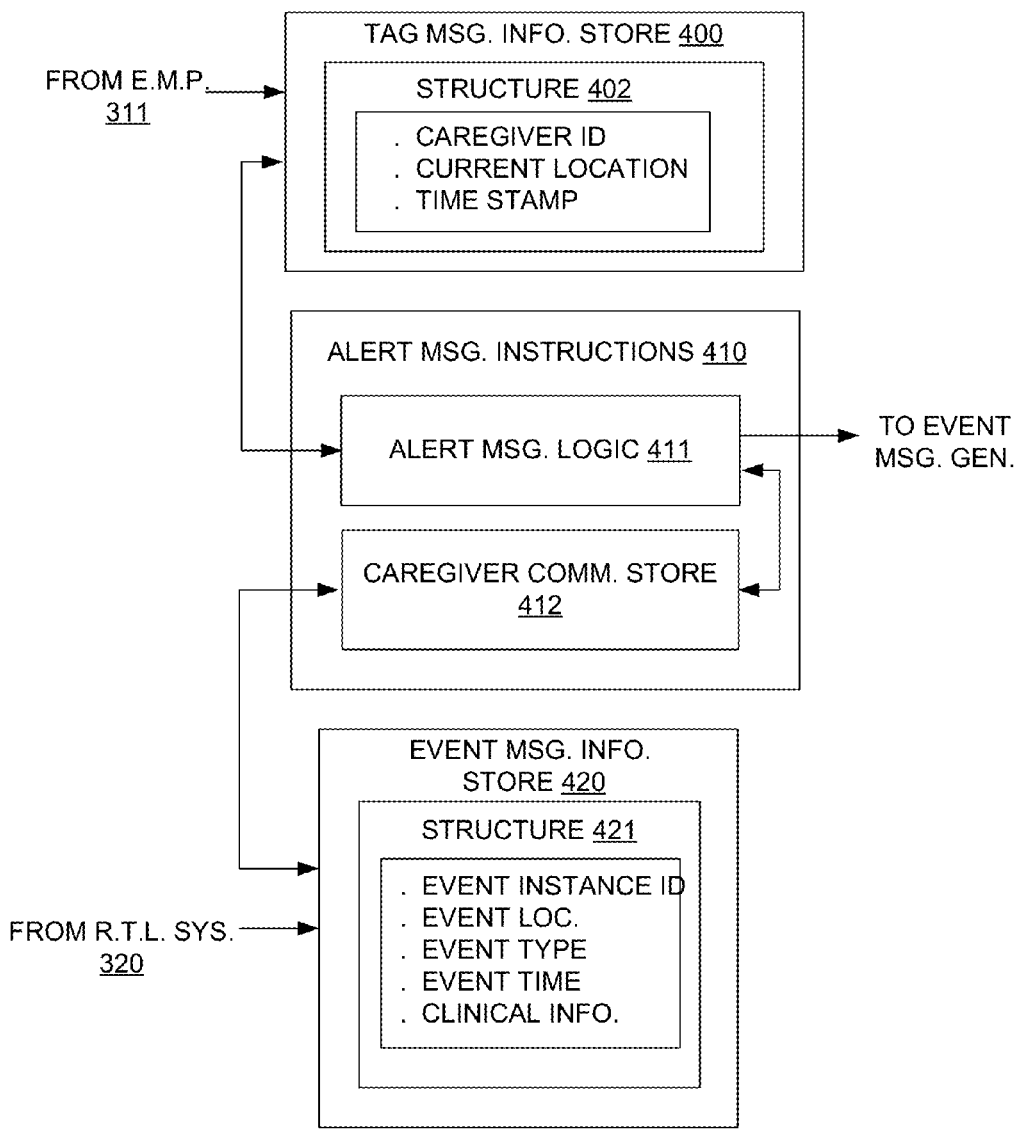
FIG. 4 illustrates functional elements of a notification function comprising an event notification system connected to the healthcare network of FIG. 3.

The notification function 312 shown in FIG. 4 comprises a store of tag message information 400, a store or event message information 420, and a set of alert message instructions 410. The notification function 312 uses the instruction 410 to operate on information in the tag message store 400 and on information in the event message store 420 to determine whether it is appropriate to generate an alert message, and if so to whom the alert is sent and what type of alert message is sent. The Tag message information store 400 can be implemented as a data structure 402 for storing the identifies of individual caregivers, their current locations (as determined by a tag detector) and current time stamp information which can be a time that an individual's RTL tag is first detected by a detector and the time that the tag is no longer detected. This structure 402 can include other information such as whether an individual is on duty or not, whether an individual is occupied with a task or not, or other information that is useful in a clinical setting. All of the tag message information can be placed into the structure 402 by a data management function (not shown) that runs in association with the ENS 310, and the structure 402 can be implemented in any format that allows it to be accessed by and operated on by the notification function 312. The event message information store 420 can be implemented as a data structure 421 for storing, among other things, a plurality of clinical event instance identities, the location of each event instance, the time that each clinical event instance starts/stops, the type of each event instance, and clinical information corresponding to each clinical event instance. All of this information can be placed into the structure 421, by a data management function (not shown) that runs in association with the ENS 310, and this structure 421 can be implemented in any format that allows it to be accessed and operated on by the notification function 312.

Continuing to refer to FIG. 4, the alert message instructions 410 comprise alert message logic 411 that uses the information stored in the structures 402 and 420 to determine if an alert message should be sent and what type of alert message should be sent, and the instructions 410 comprise a caregiver communication store 412 that has a plurality of files or records, each file having different caregiver communication information. Each caregiver communication file can be comprised of the caregiver's identity, the identities of each device associated with the caregiver (i.e., mobile, PC, tablet, laptop, other), contact information associated with each device (such as a mobile or office phone number or a network address), and configuration information for each device. Each communication device 356 associated with each individual caregiver 355 can be designated by the individual as a primary type, secondary type or other type of communication device, and according to one embodiment, the logic 411 can be designed to examine the type designation associated with each communication device to determine whether an alert is or is not sent to that device, and/or it can determine what type of an alert is sent to that device. The operation of one embodiment of the alert message logic 411 is now described with reference to FIG. 5A.

Figure 5A:
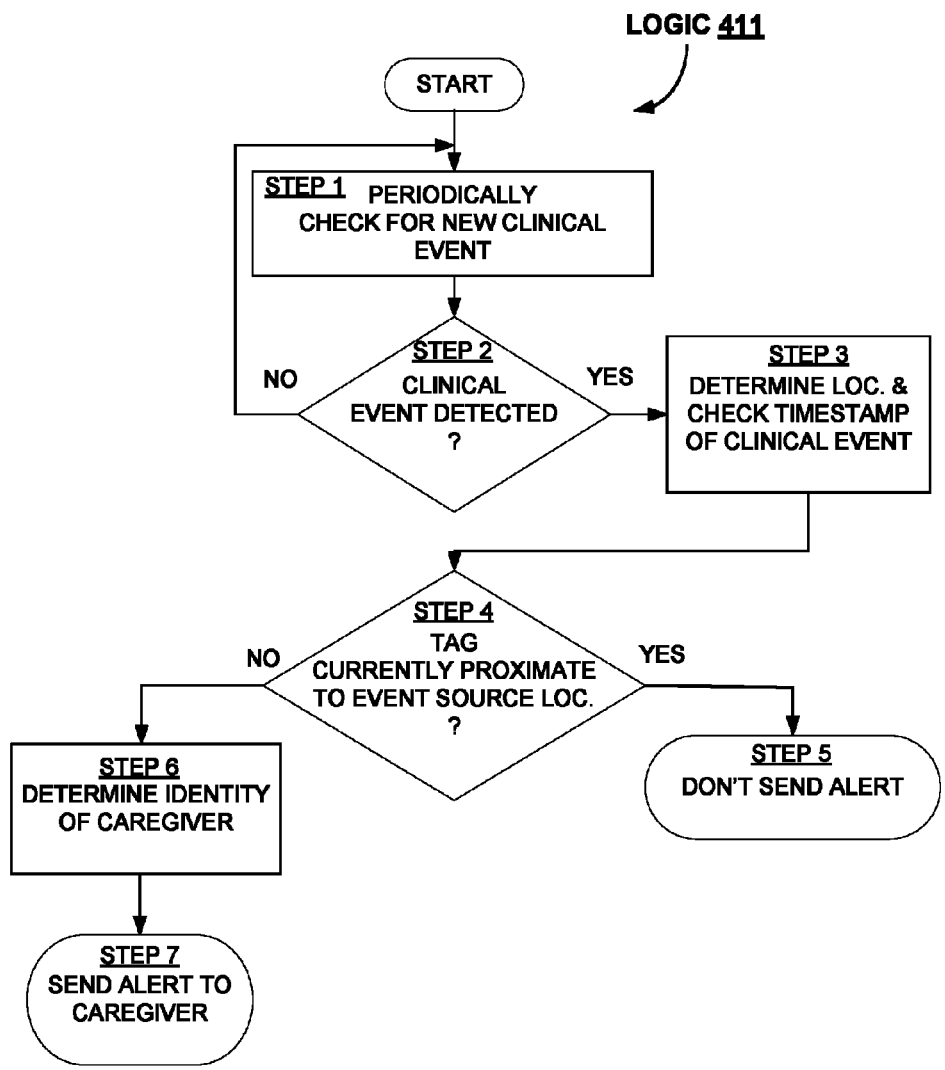
FIG. 5A is a flow diagram illustrating the operation of an embodiment of alert message logic comprising the notification function of FIG. 4.

According to the embodiment illustrated in FIG. 5A, the logic 411 is designed to operate on event store message information 420 and tag message information 400 to determine whether a caregiver is proximate to a patient during the time the patient is undergoing a clinical event, and if so, the logic 411 adjusts or modifies the normal operation of the ENS 310 to generate and send an alert message by preventing the generation of an alert message that is otherwise sent to a primary communication device assigned to that caregiver. In Step 1, the logic 411 periodically examines the event message store 420 for new or ongoing clinical events. Each event instance is uniquely identified and is maintained in the store 420 for as long as the event is active. Information associated with each instance of an event can be stored in the structure 412 (as a record or file for instance) at a memory location that can be accessed by the logic. Then, in Step 2, if logic determines that a new or ongoing clinical event is detected, in Step 3 the logic examines the event message store 420 to determine the location of the event and the latest event timestamp information. On the other hand if in Step 2 the logic does not detect a clinical event, the process returns to Step 1. Assuming that in Step 2 the logic determines that an event is active, the process proceeds to Step 4 and the logic examines the tag message store 400 to determine if a tag is proximate to the source of the clinical event during the time that the clinical event is active. In this regard, the logic can search through each caregiver record comprising the structure 402 looking for a record in which a current tag location is the same as the clinical event source location during the time the clinical event is active (i.e., it compares the timestamp information associated with the event instance stored in the structure 420 with timestamp information associated with a caregiver record stored in the tag message store 400 looking for coincidence of timestamp information). In Step 4, the logic may or may not temporarily store the identity of the caregiver associated with the caregiver record, as the operation of this embodiment does not depend upon knowing who to send an alert message to. If, in Step 4, it is determined that there is a coincidence in location and in timestamp information between the clinical event source and the tag, the logic determines that an alert message should not be generated and sent, and in Step 5 no instructions are sent to the message generator 315 that result in the generation and/or transmission of an alert message. On the other hand, if in Step 4 the logic determines that a caregiver is not proximate (in the same room, for instance) to the source of the clinical event, then the process proceeds to step 6 and the logic 411 can access a caregiver assignment store/function (not shown) typically maintained by a patient care facility that has information which can be used to determine the appropriate caregiver to alert. After determining which caregiver or caregivers should be notified of the patient clinical condition, in Step 7 an alert message is sent to the appropriate caregiver.

While the logical flow diagram in FIG. 5A shows that one branch of the logical process terminates at Step 5, this does not need to be the case. In an embodiment of the invention, the event message processor 311 in FIG. 3 can operate to periodically or continually monitor a patient monitor to determine if the clinical event that caused an event message to be sent continues to be active for longer than some pre-determined period of time or threshold time value. In this event, it may be that the caregiver proximate to the patient is too busy to attend to the clinical condition that resulted in the event message sent to the ENS 310. In the event that it is determined that a caregiver is proximate to a patient during the time that the patient is undergoing a clinical event, and the event message processor 311 determines that clinical event persists for longer than a threshold time value, then the ENS 310 can escalate the alert and operate to send a standard alert message to another, different caregiver. The event message processor 311 can be configured with the threshold time value which can be any value deemed appropriate for a particular patient, or it can be a universal value for a particular type of clinical event.

In an alternative embodiment, the logic 411 can be designed to control the alert message generator 315 to send a modified alert message to a caregiver's primary communication device. According to this embodiment, this alert message can be modified, as described earlier with reference to FIG. 3, so that it can be played by the caregiver's primary communication device in a manner that does not distract them from attending to a patient. The logic that controls the operation of this alternative embodiment is described below with reference to FIG. 5B.

The logical operation of Steps 1-4 in this alternative embodiment are the same as the embodiment described with reference to FIG. 5A, and so these step are not described again here. In Step 5, the logic 411 can examine information in the structure 402 to determine the identity of the caregiver (caregiver ID.123, for instance) that is proximate to the source of the clinical event, and then the logic can use this identity to examine a record in the communication store 412 associated with the caregiver ID.123. As described earlier with reference to FIG. 4, each caregiver communication record or file can be comprised of the caregiver's identity, the identities of each device associated with the caregiver (i.e., mobile, PC, tablet, laptop, other), contact information associated with each device (such as a mobile or office phone number or a network address), and configuration information for each device. Each communication device associated with each individual caregiver can be designated by the individual as a primary type, secondary type or other type of communication device, and according to this embodiment, the logic 411 can be designed to examine the type designation associated with each communication device to determine whether an alert is or is not sent to that device, and/or it can determine what type of an alert is sent to that device. Accordingly, in Step 6, the logic can operate on the information maintained in the caregiver's ID.123 communication record to identify a communication device designated as the caregiver's primary device and to determine whether and what type of message should be sent to the caregiver. If in Step 6 the logic determines that a modified alert message is to be sent to the caregiver's primary device, then it sends instructions to the modified alert message generation function comprising the alert message generator 315 that causes it, in Step 7, to generate and send a modified alert message to the caregiver ID.123. Alternatively, if in Step 6 the logic determines that a message should not be sent to the caregiver's primary device, it does not send any instructions to the generator 315 in Step 8.

Continuing to refer to FIG. 5B, if in Step 4 the logic determines that no caregiver, or caregiver assigned to the patient, is proximate to the clinical event source, then the process proceeds to Step 9 and the logic 411 can access a caregiver assignment store/function (not shown) associated with the healthcare network 300 that has information which can be used to determine the appropriate caregiver to alert. After determining which caregiver or caregivers should be notified of the patient's clinical condition, in Step 10 an alert message is sent to the appropriate caregiver.

We claim:

1. A method for managing alert messages generated by an event notification system, comprising:
   detecting, at a patient monitor associated with a patient, a clinical event instance and sending a clinical event message to the event notification system;
   parsing information in the clinical event message to detect a unique identity of the patient monitor and a time at which the clinical event instance is detected, and using a first map structure to determine a physical location of the patient monitor;
   detecting, at a tag detector comprising a real-time location system, the presence of a tag associated with a caregiver and detecting a time at which the tag is detected, and sending a tag message to the event notification system;
   parsing information in the tag message to determine an identity of the tag detector and to identify the time at which the tag is detected by the tag detector, and using a second map structure to determine a current physical location of the tag that the caregiver is associated with;
   comparing, at the event notification system, the current physical location of the tag and the time at which the tag is detected to the location of the patient monitor and the time at which the clinical event instance is detected, and determining that the caregiver is attending to the patient if the current tag location is proximate to the location of the patient monitor at the time that the clinical event instance is detected; and
   controlling the event notification system to not generate and send an alert message to a communication device currently worn by the caregiver.

2. The method of claim 1, further comprising the event notification system being controlled to generate and send an alert message to a communication device not currently worn by the caregiver.

3. The method of claim 1, further comprising the event notification system generating and sending an alert message to another caregiver in the event that it determines that the detected clinical event instance persists for more than a predetermined period of time.

4. The method of claim 1, wherein the event notification system is configured to recognize the type of communication device worn by the caregiver.

5. The method of claim 1, wherein the first map structure comprises the identity of the patient monitor and the physical location of the patient monitor.

6. The method of claim 1, wherein the second map structure comprises the identity of the tag detector and the physical location of the tag detector.

7. The method of claim 1, wherein the clinical event instance is a physiological characteristic of the patient detected by the patient monitor to be greater or lesser than a threshold value.

8. The method of claim 1, wherein the clinical event instance detected by the patient monitor is a patient heart rate, a respiratory rate, a temperature, or a blood oxygen level.

9. The method of claim 1, wherein the alert message comprises annunciation instructions that when operated on by the communication device cause it to play one or more tones, cause it to play some combination of tones, or cause it to vibrate at a particular frequency and intensity.

10. A healthcare network, comprising:
    one or more patient monitors operating to detect clinical event instances associated with a patient;
    a plurality of tag detectors in communication with a real-time location system, each one of the plurality of the tag detectors being positioned at different physical locations in a patient care facility and being operable to detect the presence of a tag worn by a caregiver and to detect the time that the tag is detected and to send tag detection messages to the real-time location system; and
    an event notification system that operates to receive clinical event messages from any of the one or more patient monitors and that operates to receive a tag detection message from the real-time location system, and that operates to not send an alert message to a communication device worn by the caregiver if it is determined, using information in the tag detection message and the clinical event message, that the caregiver is proximate to the patient during the time the patient is undergoing a clinical event;
    wherein the information in the clinical event message received by the event notification system comprises the identity of the patient monitor that is the source of the event message and the time that a clinical event instance is detected, and the information in the tag detection message received by the event notification system comprises the identity of a tag detector that detects the presence of the tag worn by the caregiver, the identity of the tag worn by the caregiver, and a time that the tag is detected.

11. The healthcare network of claim 10, further comprising the event notification system operating to send an alert message to a communication device not worn by the caregiver.

12. The healthcare network of claim 10, wherein the real-time location system uses the tag identity to look up a physical location of the tag in a first map structure.

13. The healthcare network of claim 12, wherein the first map structure comprises the identities and the physical location of the one or more patient monitors.

14. The healthcare network of claim 10, wherein the event notification system uses an identity of one of the one or more patient monitors to look up a physical location of the one patient monitor in a second map structure.

15. The healthcare network of claim 14, wherein the second map structure comprises an identity of one or the one or more tag detectors and a physical location of the one tag detector.

16. The healthcare network of claim 10, wherein each clinical event instance is a physiological characteristic of the patient detected by any one of the one or more patient monitors to be greater or lesser than a selected threshold value.

17. A method for managing alert messages generated by an event notification system, comprising:
    detecting, at a patient monitor associated with a patient, a clinical event instance and sending a clinical event message to the event notification system;
    parsing information in the clinical event message to identify a unique identity of the patient monitor and a time at which the clinical event instance is detected, and using a first map structure to determine a physical location of the patient monitor;

detecting, at a tag detector comprising a real-time location system, the presence of a tag associated with a caregiver and detecting a time at which the tag is detected, and sending a tag message to the event notification system;

parsing information in the tag message to determine an identity of the tag detector, an identity of the caregiver and to identify the time at which the tag is detected by the tag detector, and using a second map structure to determine a current physical location of the caregiver associated with the tag;

comparing, at the event notification system, the current location of the caregiver to the location of the patient monitor, and determining that the caregiver is attending to the patient if the current physical location of the caregiver is proximate to the physical location of the patient monitor at the time the clinical event instance is detected; and controlling the event notification system to generate and send an alert message to a communication device worn by the caregiver that when played by the communication device is recognized by the caregiver as annunciating an alert generated as the result of the clinical event instance associated with the patient to whom they are currently attending.

18. The method of claim 17, further comprising the event notification system generating and sending an alert message to another caregiver in the event that it is determined that the clinical event instance persists for more than a predetermined period of timed.

19. The method of claim 17, wherein the alert message has instructions that cause the communication device worn by the caregiver to play one or more tones, cause it to play some combination of tones, or cause it to vibrate at a particular frequency and intensity.

20. The method of claim 17, further comprising the event notification system being controlled to generate and send an alert message to a communication device not currently worn by the caregiver.

21. The method of claim 17, wherein the event notification system is configured to recognize the communication device worn by the caregiver and to recognize another communication device associated with but that is not worn by the caregiver.

22. The method of claim 17, wherein the first map structure comprises the identity of the patient monitor and the physical location of the patient monitor.

23. The method of claim 17, wherein the second map structure comprises the identity of the tag detector and the physical location of the tag detector.

24. The method of claim 17, wherein the clinical event instance is a physiological characteristic of the patient detected by the patient monitor to be greater or lesser than a threshold value.

25. The method of claim 17, wherein the clinical event instance detected by the patient monitor is a patient heart rate, a respiratory rate, a temperature, or a blood oxygen level.

* * * * *